United States Patent [19]
Swett

[11] 3,934,018

[45] Jan. 20, 1976

[54] 4,6-DIHYDRO-1,3-DIMETHYL-8-PHENYLPYRAZOLO[4,3-e][1,4]DIAZEPIN-5-(1H)-ONE AND DERIVATIVES AS ANTI-INFLAMMATORY AGENTS

[75] Inventor: Leo Ralph Swett, Waukegan, Ill.

[73] Assignee: Abbott Laboratories, North Chicago, Ill.

[22] Filed: Sept. 3, 1970

[21] Appl. No.: 69,464

[52] U.S. Cl. ............................................. 424/273
[51] Int. Cl.$^2$ ................................... A61K 31/415
[58] Field of Search ................................. 424/273

*Primary Examiner*—Stanley J. Friedman
*Attorney, Agent, or Firm*—Robert L. Niblack; Joyce R. Krei

[57] ABSTRACT

A method of relieving inflammation and its concomitant swelling, tenderness and pain by administering therapeutically effective amounts of 4,6,-dihydro-1,3-dimethyl-8-phenylpyrazolo[4,3-e] [1,4]diazepin-5-(1H)-one and the 4-alkyl derivatives thereof to a patient in need of such treatment.

4 Claims, No Drawings

4,6-DIHYDRO-1,3-DIMETHYL-8-PHENYL-PYRAZOLO[4,3-E] [1,4]DIAZEPIN-5-(1H)-ONE AND DERIVATIVES AS ANTI-INFLAMMATORY AGENTS

DETAILED DESCRIPTION OF THE INVENTION

A number of humans and animals are known to suffer from various rheumatic conditions involving inflammation, swelling, tenderness, decreased mobility, pain and fever. While there are a number of presently available anti-inflammatory agents which have been found to be effective in the symptomatic treatment of conditions such as rheumatoid arthritis, rheumatoid spondylitis and degenerative joint disease (osteoarthritis) of the hip, such agents exhibit various undesirable side effects. Thus, the search for improved anti-inflammatory agents continues. The present invention provides a method for relieving such conditions.

4,6-Dihydro-1,3-dimethyl-8-phenylpyrazolo [4,3-e] [1,4] diazepin-5-(1H)-one and its 4-alkyl derivatives have been previously reported as anti-convulsant agents (see German Patent No. 1,927,429). It has now been unexpectedly found that the compounds are orally active anti-inflammatory agents when administered to mammalian patients in need of such treatment in dosages of from 10 to 250 mg./kg. of body weight daily, preferably in divided doses.

The compounds useful in the practice of this invention are represented by the structural formula

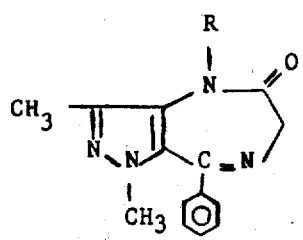

wherein R is hydrogen or $C_1$-$C_7$ alkyl.

The term "$C_1$-$C_7$ alkyl," as used herein, refers to both straight and branched chain alkyls including methyl, ethyl, n-propyl, iso-propyl, n-butyl, sec-butyl, tert-butyl, iso-butyl, n-pentyl, isopentyl, neo-pentyl, hexyl, heptyl and the like.

The anti-inflammatory activity of the compounds useful in the practice of this invention was established in the carrageenan rat paw edema test described by Winter et al, Proc. Soc. Exp. Biol. Med. 111, 554 (1962). In addition to the anti-inflammatory activity, the compounds additionally exhibit mild anti-pyretic and analgesic activity.

The compounds of this invention can be administered to, for example, arthritic patients, in dosages of from about 10 to about 250 mg./kg. of body weight daily or 600–1500 mg. daily, preferably in divided dosages, i.e., 3 to 4 times daily.

The compounds of this invention are prepared from 1,3-dimethyl-4-nitro-5-pyrazolocarboxylic acid by methods well known in the art. Generally speaking, 1,3-dimethyl-4-nitropyrazolecarboxylic acid is converted to, for example, 4,6-dihydro-1,3-dimethyl-8-phenylpyrazolo [4,3-e] [1,4] diazepin-5-(1H)-one according to the method described in German Patent No. 1.927,429 or J. Org. Chem., 27, 3788 (1962).

The preferred synthetic route for the preparation of the compounds useful in the practice of this invention is represented by the following reaction scheme.

Illustrative of compounds useful in the practice of this invention are:

4,6-dihydro-1,3-dimethyl-8-phenylpyrazolo-[4,3-e] [1,4] diazepin-5(1H)one 4,6-dihydro-8-phenyl-1,3,4-trimethylpyrazolo [4,3-e] [1,4] diazepin-5(1H)one 4,6-dihydro-1,3-dimethyl-4-ethyl-8-phenylpyrazolo-[4,3-e] [1,4] diazepin-5(1H)one The anti-inflammatory agents useful in the practice

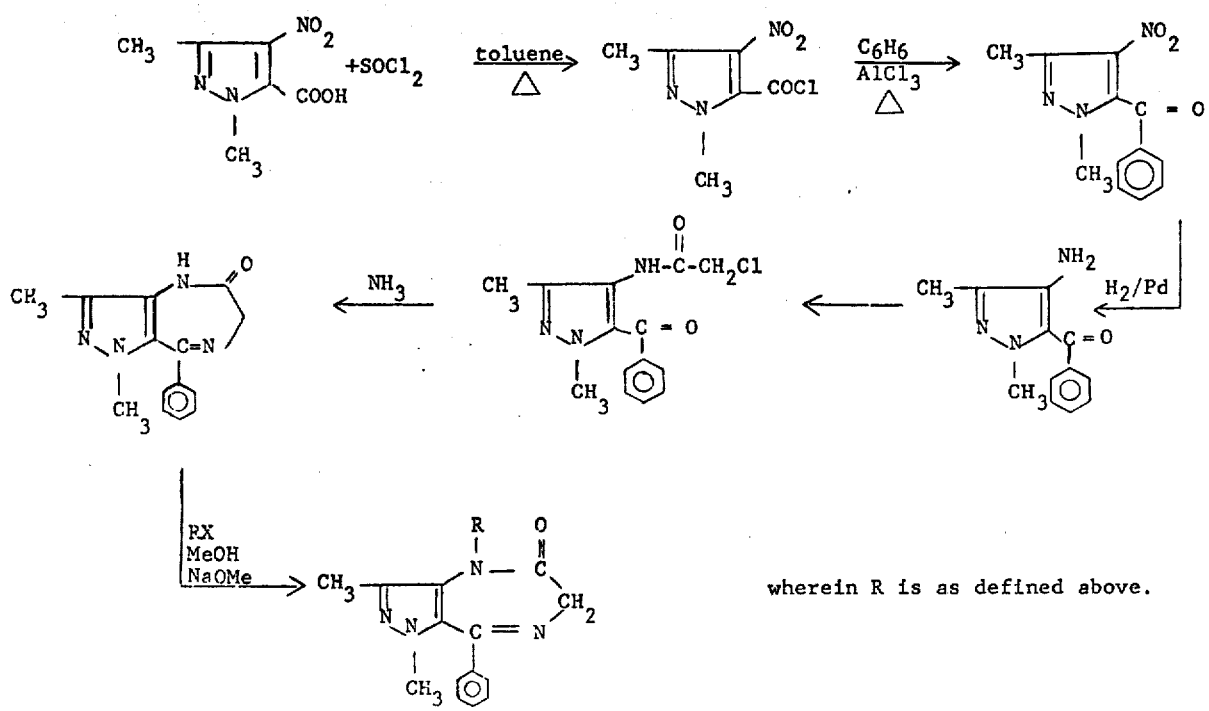

wherein R is as defined above.

of the present invention are generally formulated into pharmaceutical compositions comprising, as an active ingredient, at least one of the active agents in association with a pharmaceutical carrier or diluent. The compounds useful in the practice of the invention exhibit both oral and parenteral activity and can be formulated in dosage forms for oral, parenteral, rectal or topical administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include, pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents, and sweetening, flavoring and perfuming agents.

Preparations according to this invention for parenteral administration include sterile aqueous or non-aqueous solutions, suspension or emulsions. Examples of non-aqueous solvents or vehicles are propylene glycol, polyethylene glycol, vegetable oils, such as olive oil and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10.0 to 250 mg./kg. of body weight daily are administered to mammals to obtain effective relief of inflammation, and the concomitant pain, fever, etc.

I claim:

1. A method of relieving the symptoms of inflammation in a patient in need of such treatment by administering to said patient a therapeutically effective amount of a compound of the formula

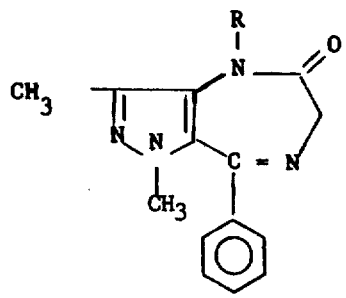

where R is hydrogen or $C_1$-$C_7$ alkyl.

2. A method in accordance with claim 1 wherein the compound is 4,6-dihydro-1,3-dimethyl-8-phenyl-pyrazolo [4,3-e] [1,4] diazepin-5-(1H)-one.

3. A method in accordance with claim 1 wherein the compound is 4,6-dihydro-8-phenyl-1,3,4-trimethyl-pyrazolo [4,3-e] [1,4] diazepin-5-(1H)-one.

4. A method in accordance with claim 1 wherein the compound is 4,6-dihydro-1,3-dimethyl-4-ethyl-8-phenylpyrazolo [4,3-e] [1,4] diazepin-5-(1H)-one.

* * * * *